(12) United States Patent  (10) Patent No.: US 8,790,361 B2
Spenciner et al.  (45) Date of Patent: Jul. 29, 2014

(54) METHODS AND DEVICES FOR CUTTING AND REMOVING TISSUE FROM A BODY

(75) Inventors: David B. Spenciner, North Attleboro, MA (US); Mehmet Z. Sengun, Canton, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 13/478,240

(22) Filed: May 23, 2012

(65) Prior Publication Data

US 2013/0317532 A1  Nov. 28, 2013

(51) Int. Cl.
 *A61B 17/32* (2006.01)

(52) U.S. Cl.
 USPC ........................................... 606/171

(58) Field of Classification Search
 USPC .......... 606/167, 169, 170, 171; 600/562, 564, 600/565, 566, 567, 568
 See application file for complete search history.

(56) References Cited

U.S. PATENT DOCUMENTS

| | | | |
|---|---|---|---|
| 4,167,944 A * | 9/1979 | Banko | 606/107 |
| RE33,258 E * | 7/1990 | Onik et al. | 604/22 |
| 5,527,332 A | 6/1996 | Clement | |
| 5,776,092 A | 7/1998 | Farin et al. | |
| 5,782,849 A | 7/1998 | Miller | |
| 5,904,681 A | 5/1999 | West, Jr. | |
| 5,911,701 A | 6/1999 | Miller et al. | |
| 6,451,022 B2 | 9/2002 | Dinger et al. | |
| 2002/0029060 A1 | 3/2002 | Hogendijk | |
| 2008/0033465 A1 | 2/2008 | Schmitz et al. | |
| 2008/0103504 A1 | 5/2008 | Schmitz et al. | |
| 2010/0298835 A1 | 11/2010 | Ralph et al. | |
| 2013/0060272 A1 | 3/2013 | Thistle | |

FOREIGN PATENT DOCUMENTS

| | | |
|---|---|---|
| EP | 125070 A2 | 11/1984 |
| EP | 1832235 A1 | 9/2007 |
| WO | 00/62683 A1 | 10/2000 |

OTHER PUBLICATIONS

Extended European Search Report for Application No. 13169003.4, mailed Jul. 31, 2013 (6 pages).

* cited by examiner

*Primary Examiner* — Jonathan W Miles

(57) ABSTRACT

Methods and devices are provided for cutting and removing tissue from a body. In one exemplary embodiment, a surgical device is provided having a suction shaft and a cutting assembly. The suction shaft can have an inner passageway configured to receive tissue. The cutting assembly can include an outer shaft having at least one opening formed in a sidewall thereof configured to receive tissue. The cutting assembly can be configured to mate with the suction shaft, and it can include a cutting element configured to move relative to the opening to cut tissue disposed through the opening. Suction can be applied to cause the cut tissue to flow proximally through the suction shaft and away from the cutting assembly.

17 Claims, 9 Drawing Sheets

FIG. 8
FIG. 9
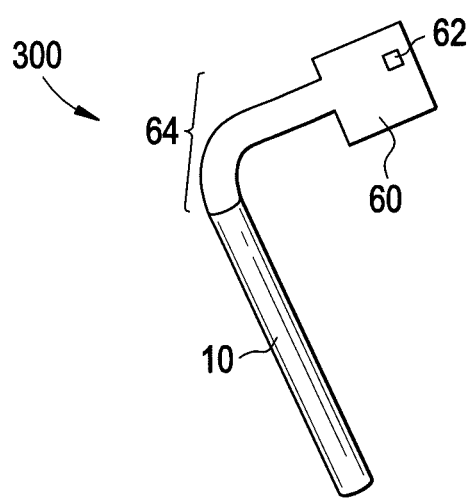
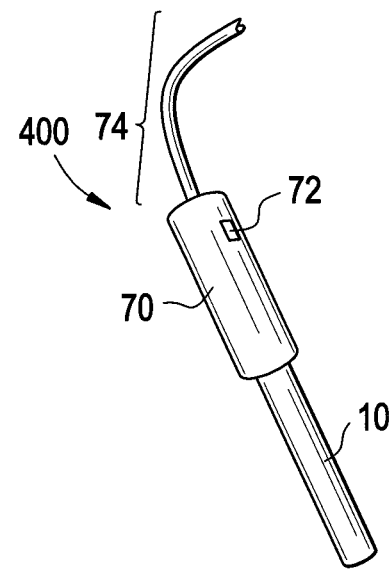
FIG. 10
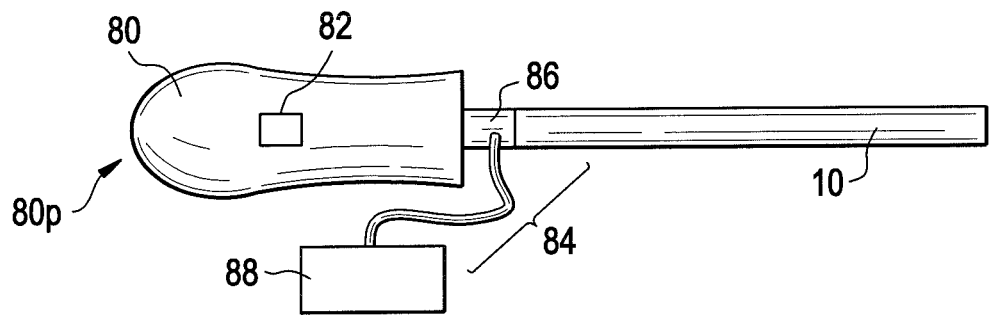

METHODS AND DEVICES FOR CUTTING AND REMOVING TISSUE FROM A BODY

FIELD OF THE INVENTION

The present invention relates generally to methods and devices for cutting and removing tissue from a body, and in particular, to arthroscopic shavers and methods of using the same.

BACKGROUND OF THE INVENTION

Arthroscopy is a minimally invasive surgical technique for removing diseased or damaged tissue from intra-articular regions of the body, such as the shoulder, hip, wrist, knee, and spine. Arthroscopic shavers can be used to remove bone, cartilage, and other soft tissue from a patient's joint with less surgical trauma to the joint than conventional surgical techniques. Typically, an arthroscopic shaver is an electro-mechanical device that includes a hand piece and an elongate shaft that houses a cutting assembly. The cutting assembly can be positioned at a distal portion of the elongate shaft and can include a rotatable and/or translatable cutting element for cutting tissue. Typically, the cutting element is cannulated so that fluid and tissue can pass through it. In some cases, the hand piece is releasably mated to the elongate shaft so that the cutting assembly can be disposed of after each use and the hand piece can be reused. During an arthroscopic procedure, the distal end of the shaft is inserted into a small incision formed in a patient. Suction is applied to the shaver to cause bodily tissue and associated fluids to flow through the cutting assembly and out through a proximal end of the hand piece where the tissue and fluids can be collected in a waste collection container.

In view of the benefits of minimally invasive procedures, it would be desirable to reduce the size profile of shavers to allow arthroscopic shavers to be inserted into the body through smaller access portals. However, cutting elements of current shavers are usually cannulated to allow fluid and excised tissue to pass through, and this limits the effectiveness of such shavers when the size is reduced. More specifically, as the diameter of the cutting element and the elongate shaft are reduced, the components become less stiff and cut tissue can become trapped in the cutting assembly. Even a small mass of tissue can impart a transverse load on the cutting element, which can cause tissue to travel in-between the moving and stationary components and/or cause the cutting surfaces to prematurely wear. This can result in binding and/or ineffective cutting.

The configurations of current devices restrict the ability to reduce the size profile of these shavers in other ways. For example, in devices where the cutting assembly extends proximally through the device, tissue and cut fluid also flows proximally through the cutting assembly such that the space for tissue/fluid to be suctioned out is limited by the diameter of the outer shaft and the diameter of the cutting assembly. At the same time, it is important that the pathway for tissue and fluid flow be large enough to enable efficient removal of bodily matter and/or to enhance visualization of the surgical site.

Accordingly, there remains a need for improved methods and devices for cutting and removing tissue from a body.

SUMMARY OF THE INVENTION

Various surgical devices are provided herein. In one embodiment, a surgical device is provided that includes a suction shaft and a cutting assembly. The suction shaft can have an inner passageway extending therethrough between proximal and distal ends thereof, and the suction shaft can be configured to couple to a vacuum source to apply suction through the inner passageway. The cutting assembly can include an outer shaft and an inner shaft. More specifically, the outer shaft can have an inner passageway extending therethrough between proximal and distal ends of the outer shaft, and the outer shaft can have a window formed through a sidewall adjacent to the distal end. The inner shaft can have a cutting element at a distal end, and the inner shaft can be slidably disposed within the outer shaft such that the cutting element is movable relative to the window. This can allow tissue extending through the window and into the inner passageway to be cut by the cutting element. The distal end of the outer shaft can be configured to mate with the distal end of the suction shaft such that, when suction is applied through the passageway in the suction shaft, tissue cut by the cutting element is suctioned out of the distal end of the outer shaft and into the distal end of the suction shaft and can flow in a proximal direction through the inner passageway of the suction shaft.

The device can vary in any number of ways. For example, the inner shaft can be non-cannulated. The cutting element can be formed on a distal-facing surface of the inner shaft. The device can also include a suction mechanism configured to apply a suction force within the inner passageway of the suction shaft to cause the tissue cut by the cutting element within the inner passageway to flow in the proximal direction through the inner passageway. The window on the outer shaft can also include a cutting feature formed thereon. More specifically, the cutting feature can be formed on a distal edge of the window such that the cutting element faces the cutting feature when the cutting element moves within the outer shaft. For another example, an outer diameter of the outer shaft can be less than about 2 mm, and an outer diameter of the suction shaft can be less than about 2 mm. The suction assembly can be mated to the cutting assembly in various ways. For example, the distal end of the outer shaft can be receivable within the distal end of the suction shaft for mating the suction shaft and the outer shaft.

The surgical device can be configured to cut tissue in a variety of ways. For example, in one embodiment the cutting element can be configured to move longitudinally within the inner passageway along a longitudinal axis of the outer shaft to cut tissue extending through the window and into the inner passageway. In another embodiment, the cutting element can be configured to rotate within the inner passageway about a longitudinal axis of the outer shaft to cut tissue extending through the window and into the inner passageway.

In another aspect, a surgical method is provided. In one embodiment, the method can include advancing a cutting assembly into a body of a patient, advancing a suction shaft into a body of the patient, mating a distal end of the cutting assembly with a distal end of the suction shaft, applying a suction force through an inner passageway of the suction shaft to suction tissue through a window in the cutting assembly, and actuating the cutting assembly to cut the tissue suctioned through the window. The cut tissue is suctioned out of the distal end of the cutting assembly and through the inner passageway in the suction shaft such that the cut tissue flows proximally through the inner passageway of the suction shaft.

The surgical method can include a variety of modifications. For example, the suction shaft can be advanced through a first access opening in the patient, and the cutting assembly can be advanced through a second access opening in the patient. In one embodiment, the first access opening can be on a first side of a joint of the patient, and the second access opening can be on a second, opposite side of the joint. In another embodiment, mating a distal end of the cutting assembly with a distal end of the suction shaft can include inserting the distal end of the cutting assembly into the distal end of the suction shaft.

The cutting element can move in any number of ways. For example, in one embodiment actuating the cutting assembly can move the cutting element along a longitudinal axis of the inner shaft of the cutting assembly to cut tissue extending through the window in the cutting assembly. In another embodiment, actuating the cutting assembly can rotate the cutting element about a longitudinal axis of the inner shaft of the cutting assembly to cut the tissue extending through the window in the cutting assembly.

BRIEF DESCRIPTION OF THE DRAWINGS

The invention will be more fully understood from the following detailed description taken in conjunction with the accompanying drawings, in which:

FIG. 8 is a perspective view of another embodiment of a suctioning assembly, including a suction shaft and a control unit configured to apply suction to the shaft;

FIG. 9 is a perspective, partial view of another embodiment of a suctioning assembly that includes a suction shaft and a hand piece;

FIG. 10 is a perspective, partial view of another embodiment of a suctioning assembly that is configured to divert tissue and fluid away from a hand piece;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various methods and devices are provided for cutting and removing tissue from a body. In general, a surgical device is provided that can remove tissue from within a patient's body and/or reshape the patient's anatomy. In an exemplary embodiment, a device is provided having a cutting assembly configured to cut tissue and a suctioning assembly configured to remove the cut tissue from a surgical site. The suction assembly and the cutting assembly can be separate, at least at the distal end portion, to allow tissue cut by the cutting assembly to be suctioned and removed by the suction assembly, rather than being removed from the patient through the cutting assembly. For example, in one exemplary embodiment a distal end of the cutting assembly can be configured to couple to a distal end of the suction assembly. The cutting assembly can be activated to cut tissue, and suction can be applied to draw the cut tissue proximally though the suction assembly. Because tissue cut by the cutting element can be removed through the suction assembly, the cutting assembly can have a reduced diameter. In particular, positioning the cutting element opposite to a direction of the flow of cut tissue, diameters of the suction assembly and the cutting assembly can be relatively small (e.g., less than about 2 mm in diameter) and appropriate for use in arthroscopic surgery, without compromising the effectiveness of cutting and suctioning of tissue. The suction assembly and the cutting assembly can also be separately introduced into a patient and/or inserted through different access portals, thus allowing the device to more optimally approach a surgical site, such as a joint. The use of two shafts can also facilitate cleaning of the device such that one or both of the shafts can be reused for the same patient or for a different patient. While in an exemplary embodiment the device can be used to cut and suction soft tissue, e.g. cartilage, the device can additionally or alternatively be configured to cut and suction hard tissue, e.g. bone, as discussed further below. The device can also be configured to suction fluid, which can improve a user's visualization of the surgical site.

Figure 1:
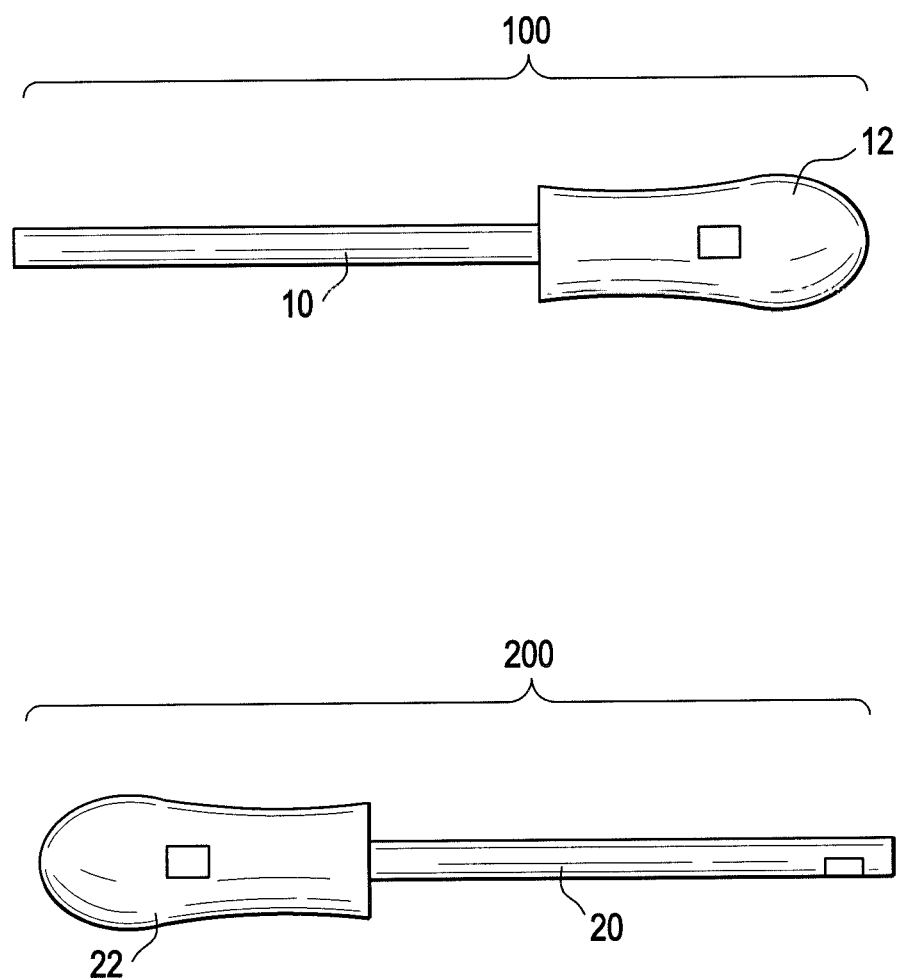
FIG. 1 is a perspective view of a device that includes a cutting assembly and a suctioning assembly, according to one exemplary embodiment.

FIG. 1 illustrates one exemplary embodiment of a device having a suctioning assembly 100 and a cutting assembly 200. In general, the suctioning assembly 100 can include a suction shaft 10 and a hand piece 12, and the cutting assembly 200 can include an outer shaft 20 and a hand piece 22. As will be discussed in greater detail below, the cutting assembly 100 can house a cutting element (not shown) configured to cut tissue, while the suction assembly 200 can be configured to suction cut tissue through the suction shaft 10 and away from the cutting assembly 100. The components of the cutting assembly 200 will be discussed first, followed by a description of the components of the suctioning assembly 100.

As mentioned above, the cutting assembly 200 can include the hand piece 22. The proximal end 20p of the outer shaft 20 can be coupled to a hand piece 22, which can house a motor and an actuator 26, e.g., a button, switch, lever, etc. Engagement of the actuator 26 can cause an inner shaft 31 to move within the inner passageway 24 of the outer shaft 20, as will be discussed below. In one embodiment, a single actuator can be used to effect rotation and translation of the cutting element. In other embodiments, the rotation and translation can be separately controlled using two or more actuators.

Figure 2:
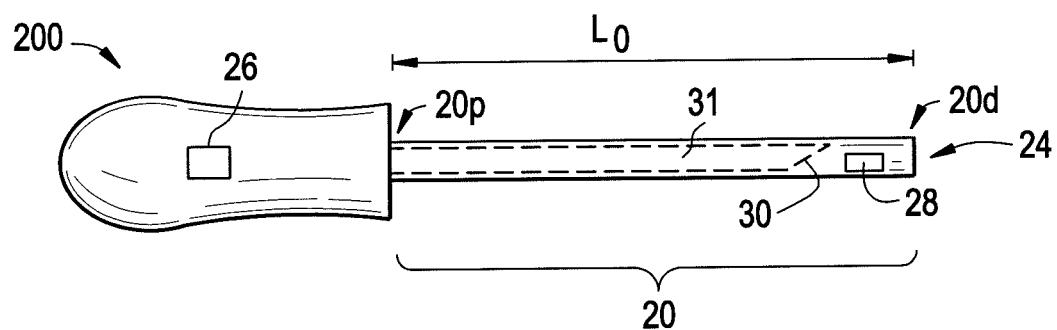
FIG. 2 is a perspective view of the cutting assembly of FIG. 1, showing a window formed in an outer shaft and an inner shaft positioned within the outer shaft.

The outer shaft 20 of the cutting assembly 200 can have various sizes, shapes, and configurations. As shown in FIG. 2, the outer shaft 20 can have a proximal end 20p, a distal end 20d, and an inner passageway 24 extending therethrough between proximal and distal ends. The outer shaft 20 can have a cylindrical shape, and thus, the outer shaft can have a substantially circular cross-sectional shape. A cross-section of the outer shaft 20 can be shaped in other ways. For example, a cross-sectional shape of the outer shaft 20 can be ovular, polygonal, rectangular, etc., and this can facilitate mating and cutting. The outer shaft can have any longitudinal length. For example, the outer shaft 20 can have a length such that when a distal end 22d of the outer shaft 20 is inserted in a patient, the proximal end 20p of the shaft can be positioned external to a patient's body to facilitate manipulation of the shaft 20. In an exemplary embodiment, the outer shaft has a length $L_o$ in a range of about 50 to 200 mm. The outer shaft 20 can be formed from one or more materials, such as plastic, polymer, and metal. In one embodiment, the outer shaft 20 can be substantially flexible along its entire length. In another embodiment, a first portion of the outer shaft 20 can be flexible while a second portion can be substantially rigid, such as to facilitate mating of the outer shaft 20 with the suction shaft 10 (not shown). In other embodiments, the outer shaft can be rigid along its entire length. The outer shaft 20 can have a substantially constant diameter, as in the illustrated embodiment. In another embodiment, a diameter of an outer shaft can decrease distally such that a distal portion of the outer shat has a diameter less than a diameter of a proximal portion of the outer shaft. This can be desirable, for example, when an inner shaft moves within relative to the outer shaft, as discussed further below, because the distal tapering of the outer shaft can inhibit translation of the inner shaft relative to the outer shaft and prevent a cutting element of the inner shaft from exiting the outer shaft, thereby helping to keep the cutting element adjacent a window formed through the outer shaft.

Figure 3:
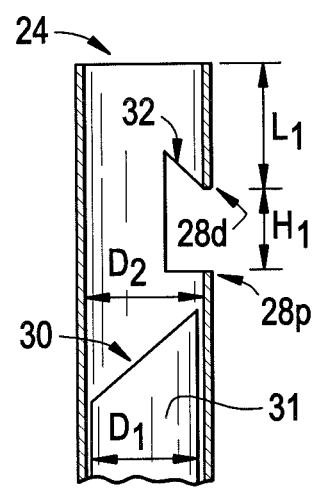
FIG. 3 is a cross-sectional, partial view of a distal end of the cutting assembly of FIGS. 1 and 2.

As shown in FIGS. 1-3, the outer shaft 20 can have at least one window, cut-out, or opening, 28, generally referred to herein as a "window," formed in a sidewall thereof. The window 28 can be configured to receive tissue therethrough to allow the tissue to pass into the inner passageway 24 of the outer shaft 20. In particular, the window 28 can extend through a wall of the outer shaft 20, and thus, can be in communication with the inner passageway 24 such that tissue can be received in the window 28 and can be drawn into the inner passageway 24. In the illustrated embodiment, the window 28 can have a substantially rectangular shape, with a height $H_1$ extending in a proximal-distal direction that is greater than a width extending radially around the outer shaft 20. A person skilled in the art will appreciate that the window 28 can have other shapes, such as circular, ovular, square, trapezoidal, etc. In the illustrated embodiment, a cutting feature 32 can be formed on a distal end 28d of the window 28 that can have a sharpened or pointed edge configured to pierce tissue, also referred to as a "stationary cutting element." The stationary cutting element 32 can include an angled edge that extends between outer and inner surfaces of the outer shaft 20 and is angled from an outer surface of the shaft 20 toward the distal end 20d of the shaft, on inner surface of the shaft 20 to form a sharp cutting edge. In this embodiment, the stationary cutting element 32 can be opposed to the movable cutting element 30, as discussed further below. A distal end 28d of the window 28 can have a substantially blunt edge that is oriented radially along the outer shaft 20. In general, the window 28 can be positioned at various locations along the outer shaft 20. For example, the window 28 can be located proximal to the distal end 20d of the shaft 20, at a distance $L_1$ from the distal end 20d of the shaft 20. By way of non-limiting example, the distance $L_1$ can be in a range of about 5 to 25 mm, e.g., about 5 to 10 mm. This can help ensure that the outer shaft 20 can mate to the suction shaft 10 without blocking the window 28, and thus, can provide space for various mating features for joining the shafts.

In another embodiment, a plurality of windows can be formed at various locations on the outer shaft. For example, the windows can be spaced along the proximal-distal length of the shaft, and/or the windows can be spaced radially about the shaft. Any number of windows can be positioned at various locations on the outer shaft.

The cutting assembly can include various components for cutting tissue. For example, FIG. 2 shows one embodiment of a cutting assembly 200 that includes the inner shaft 31 disposed within an outer shaft 20. The inner shaft 31 can be slidably and/or rotatably disposed within the outer shaft 20, as will be discussed below. The inner shaft 31 can have various sizes, shapes, and configurations. As shown in FIGS. 2-3, the inner shaft 31 can be non-cannulated or solid and can have a generally cylindrical shape that is sized to fit within the inner passageway 24 of the outer shaft 20. A diameter $D_1$ of the inner shaft 31 can be complementary to a diameter $D_2$ of the outer shaft 20 to allow the inner shaft 31 to move relative to the outer shaft 20. More specifically, the diameter $D_1$ of the inner shaft 31 can be small enough to permit the inner shaft 31 to be rotated and/or translated within the outer shaft 20 without producing undue frictional forces. At the same time, the diameter $D_1$ of the inner shaft 31 can be large enough to prevent tissue and/or fluid from passing between an outer surface of the inner shaft 31 and an inner wall of the outer shaft 20, which could cause clogging and/or inhibit movement of the inner shaft 31 and thereby inhibit efficient removal of tissue from a body. By being non-cannulated or solid, the inner shaft 31 can exhibit relatively great stiffness even when having a relatively small diameter. In general, the diameter $D_1$ of the inner shaft 31 can be in a range of about 85 to 99 percent, e.g., about 95 to 99 percent, of the inner diameter $D_2$ of the outer shaft 20.

Although the inner shaft 31 can have a shape corresponding to a shape of the outer shaft 20, e.g., each having generally cylindrical shapes with generally circular cross-sections, as mentioned above, the inner shaft 31 can have a shape differing from the shape of the outer shaft 20. In one embodiment, an inner shaft can have a cross-sectional shape, e.g., a non-circular cross-sectional shape, at least in a distal portion of the inner shaft that differs from a cross-sectional shape, e.g., generally circular, of an outer shaft in which the inner shaft is configured to be mated by being disposed therein. In this way, the mating of the inner shaft with an interior of the outer shaft, e.g., an inner lumen of the outer shaft, can limit motion of the inner shaft to longitudinal translation such that rotation of the inner shaft within the outer shaft is limited or prevented, which can help ensure that a cutting element of the inner shaft aligns with a cutting edge of the outer shaft. The non-circular cross-sectional shape of the inner shaft can be a polygon, e.g., a rectangle, a hexagon, etc., or can be an irregular shape. An inner shaft having a non-circular cross-sectional shape can be keyed to an outer shaft, which can help facilitate longitudinal translation of the inner shaft within the outer shaft, thereby helping to ensure that a cutting element of the inner shaft aligns with a cutting edge of the outer shaft. The inner and outer shafts can be keyed together in a variety of ways, as will be appreciated by a person skilled in the art, such as by having a groove, e.g., a longitudinal track, formed in one of the inner and outer shafts and a complementary protrusion, e.g., a longitudinal rail or a protruding pin, formed on the other of the inner and outer shafts that is configured to slidably mate to the track or groove. In another embodiment, in which an inner shaft is configured to rotationally translate within an outer shaft, the inner shaft can be configured to have limited longitudinal translation within the outer shaft so as to help ensure that a cutting element of the inner shaft aligns with a cutting edge of the outer shaft.

Figure 4:
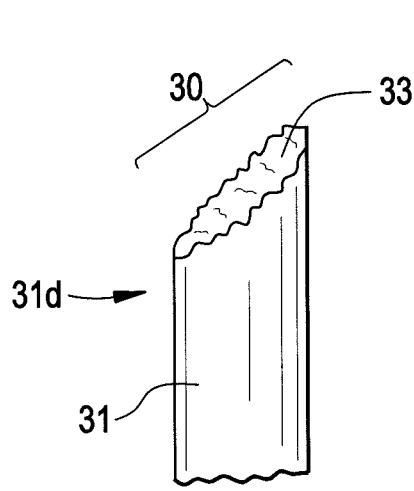
FIG. 4 is a side view of a distal end of the inner shaft of FIG. 2 having a cutting element formed thereon.
Figure 5:
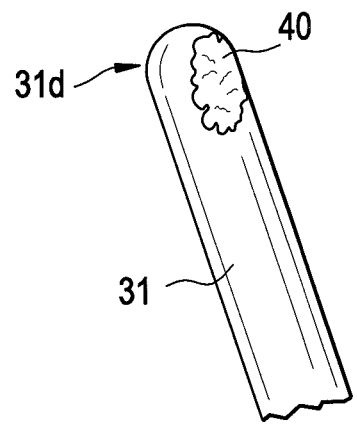
FIG. 5 is a side view of another embodiment of a cutting element.
Figure 6:
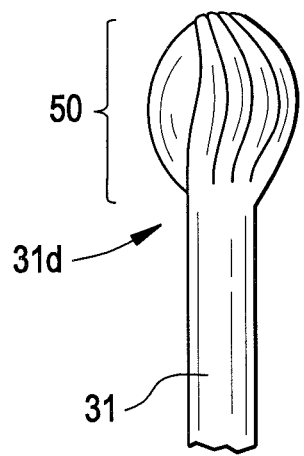
FIG. 6 is a side view of yet another embodiment of a cutting element.

Referring again to the embodiment of FIG. 1, the cutting assembly can also include a cutting element configured to cut tissue by rotating and/or translating relative to the outer shaft. In one embodiment, the cutting element 30 can be formed on the distal end 31d of the inner shaft 31. This is shown, for example, in FIGS. 2-3. The cutting element can vary in a number of ways. As shown in FIG. 4, which is a more detailed view of the cutting element 30 of FIGS. 2-4, the cutting element 30 can have a plurality of surface features 33 or serrations configured to cut tissue. In the illustrated embodiment, for example, the cutting element 30 has a terminal end surface that forms a cutting edge and that is angled at about 45 degrees relative to a longitudinal axis of the inner shaft 31. However, the cutting edge can have any angle, and in an exemplary embodiment the angle can be in a range of about 20 to 60 degrees. In general, steeper angles can produce a more sharply pointed cutting edge that can more easily pierce tissue. Another exemplary cutting element 40 is shown in FIG. 5. In this embodiment, the cutting element 40 can be in the form of a depression formed in a sidewall near the distal end 31d of the inner shaft 31 with surface features that can facilitate cutting of tissue. Exemplary features include serrations, teeth, etc. In another embodiment, the cutting element can be a bone burr 50 mated to the distal end 31d of the inner shaft 31, as shown in FIG. 6. The bone burr 50 can have a generally spherical surface with a plurality of ridges, flutes, or threads extending therearound. The bone burr 50 can be formed from a substantially rigid material configured to cut bone.

Figure 7:
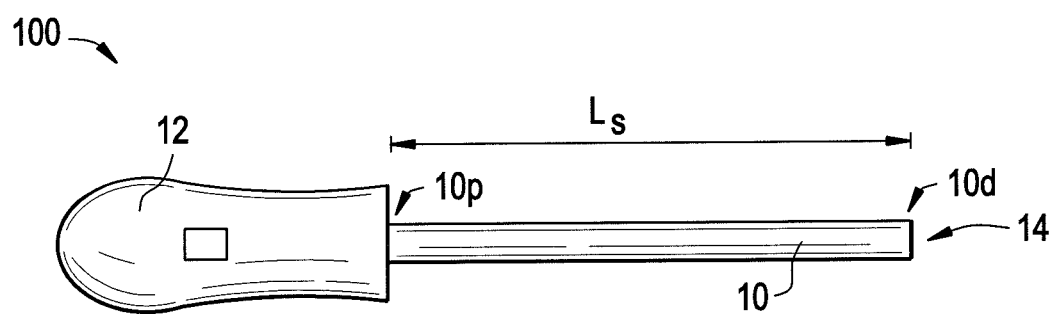
FIG. 7 is a perspective view of the suctioning assembly of FIG. 1.

As shown in FIGS. 1 and 7, in one embodiment the suction assembly 100 can include the hand piece 12 and the suction shaft 10. The hand piece 12 of the suction assembly can allow a user to grasp the device and to control suction applied to the suction shaft 10. Similar to the hand piece 22 of the cutting assembly, the hand piece 12 can have one or more actuators that can be depressed or otherwise engaged to activate a vacuum source (not shown) disposed in or coupled to the hand piece 12 for applying suction through the suction shaft 10.

The suction shaft 10 of the suction assembly 100 can have various sizes, shapes, and configurations. Similar to the outer shaft 20, the suction shaft 10 can have a proximal end 10p, a distal end 10d, and an inner passageway 14 extending therebetween. In one embodiment, the suction shaft 10 can have a cylindrical shape, and thus, the suction shaft 10 can have a substantially circular cross-section. A cross-section of the suction shaft 10 can be shaped in other ways. For example, a cross-section of the suction shaft can be ovular, polygonal, rectangular, etc. The suction shaft 10 can have any longitudinal length. For example, the suction shaft 10 can have a length such that when a distal end of the device 100 is inserted in a patient, the proximal end 10p of the suction shaft 10 can be positioned external to a patient's body to facilitate manipulation of the suction shaft 10 and to allow the proximal end 10p of the shaft to be coupled to a vacuum source. In an exemplary embodiment, the suction shaft has a length $L_s$ in a range of about 50 to 200 mm. The suction shaft 10 can be formed from one or more materials, such as plastic, polymer, and metal. In one embodiment, the suction shaft 10 can be substantially flexible along its entire length. In another embodiment, a portion of the suction shaft 10 can be flexible while the remaining portion can be substantially rigid. For example, a distal portion of the suction shaft 10 can be substantially rigid to facilitate mating with the outer shaft 20 of the cutting assembly 200. In other embodiments, the suction shaft 10 can be rigid along its entire length.

FIG. 8 illustrates another embodiment of a suction assembly 300 that includes the suction shaft 10 and a control unit 60. As shown, the control unit 60 can have at least one actuator 62, such as a button, switch, etc., disposed thereon for controlling suctioning applied to the suction shaft 10. In this embodiment, the proximal end 10p the suction shaft 10 can be removably and replaceably mated to a tube 64 that extends from the control unit 60, such as to allow the suction shaft 10 to be reconditioned and reused after a surgical procedure. In general, an inner diameter of the tube (not shown) can be at least as large as the inner diameter $D_5$ of the suction shaft 10 to allow cut tissue and fluid to pass therethrough without clogging the suctioning assembly 300. The control unit 60 can be mated to the suction shaft 10 using various techniques known in the art, such as by a slip-fit. The suctioned tissue and/or fluid can be collected in various ways, such as in a waste collection container (not shown) disposed in or coupled to the control unit 60. In addition, the waste collection container could be removed from the control unit 60 to allow the device 300 to be reused over multiple procedures. This can eliminate the need for built-in fluid management systems, and thus can allow the device 300 to be used in a variety of settings, such as in a physician's office. Because the suction shaft 10 can be connected to the control unit 60 using a length of the tube 64, the control unit 60 can be disposed at a distance away from a surgical site, such as on a nearby surgical table.

FIG. 9 illustrates another embodiment of a suctioning assembly 400. As shown, the suctioning assembly 400 generally includes a hand piece 70 and a suction shaft 10. The hand piece 70 can be configured to be grasped by a user and it can include various components for controlling suctioning applied through the suction shaft 10. The hand piece 70 can include an actuator 72, e.g. a rotatable lever, for engaging a valve that controls suction applied to the shaft 10. A tube 74 can extend from a proximal end 70p of the hand piece 70 for receiving cut tissue and fluid, and the tube 74 can be in fluid communication with a waste collection container (not shown) and/or a fluid management system known in the art. A person skilled in the art will appreciate that hand piece can have a variety of configurations, and various hand piece assemblies known in the art can be used.

FIG. 10 illustrates another embodiment of a suction assembly 500. In this embodiment, instead of coupling a proximal end of a hand piece to a vacuum source, an opening 86 can be formed distal to the hand piece 80. In particular, the opening 86 can be formed in the suction shaft 10 and tube 84 can extend therefrom that can be connected to a suction source 88 such that when the suction source 88 is activated using an actuator 82, tissue and fluid can flow through the tube 84 and into a waste collection container (not shown). This can prevent fluid and tissue from entering the hand piece 80, which can reduce the risk that fluid and tissue remains trapped inside of the hand piece 80 even after cleaning and/or sterilization procedures are performed. Exemplary embodiments are shown, for example, in U.S. application Ser. No. 13/223,821 filed on Sep. 1, 2011 and entitled "Tissue Shavers," which is hereby incorporated by reference in its entirety.

A person skilled in the art will appreciate that the various suction assemblies discussed herein can have a variety of configurations, and can include or can be coupled to various processing and/or collection devices. For example, the cut tissue can be delivered to a scaffold for implantation. Moreover, the suction assemblies can include any number of features, such as a partially or fully rigid and/or flexible shaft.

Figure 11A:
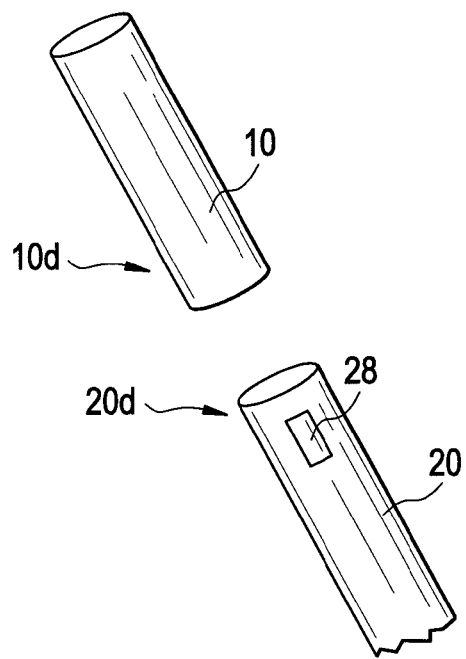
FIG. 11A is a perspective, partial view of a distal end of the suction shaft positioned near a distal end of the outer shaft.
Figure 11B:
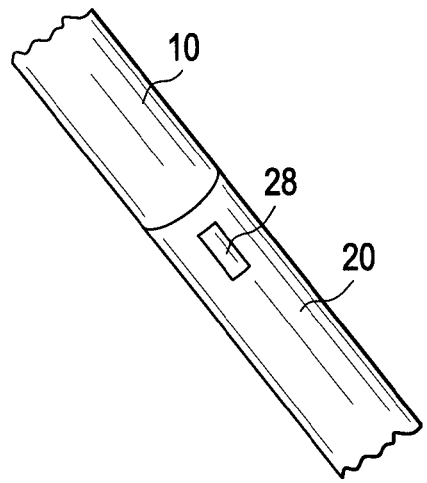
FIG. 11B is a perspective, partial view of the distal ends of the shafts of FIG. 11A mated together.
Figure 11C:
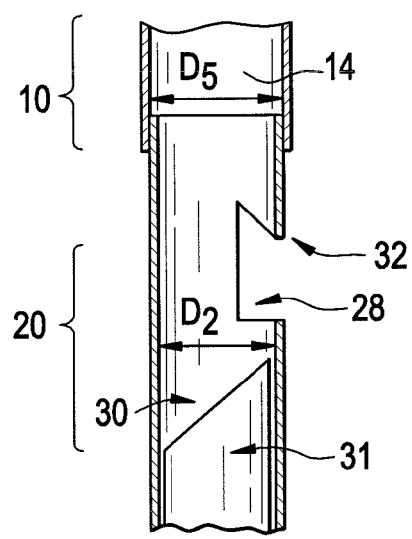
FIG. 11C is a cross-sectional, partial view of the shafts of FIG. 11B showing the inner shaft disposed in the outer shaft of the cutting assembly.

As mentioned above, the suctioning assembly 100 and the cutting assembly 200 can be mated together either prior to or following advancing of the shafts 10, 20 into a surgical site. FIG. 11A shows the shafts 10, 20 positioned in proximity, prior to mating, while FIGS. 11B-11C show the shafts 10, 20 mated together. The suction shaft 10 and the outer shaft 20 can be mated using various techniques known in the art. This can include, for example, using magnets, using mechanical mating features such as twist-lock, morse-taper, or remote quick-connect, or using other mating techniques known in the art. Additionally or alternatively, the suctioning force applied to the suction shaft 10 can help maintain the shafts 10, 20 in the mated configuration. In the illustrated embodiment, the suction shaft 10 and the outer shaft 20 can be mated using a slip-fit in which the outer shaft 20 of the cutting assembly 200 is inserted into the distal end 22 of the suction shaft 10. Ends of the shafts 10, 20 can overlap, as shown in FIG. 11C. In embodiments where the outer shaft 20 has a diameter $D_2$ that is larger than the diameter $D_S$ of the suction shaft 10, for example, an inner surface of the outer shaft 20 can be positioned to extend over an outer surface of the suction shaft 10. In this embodiment, friction between an outer surface of the outer shaft 20 and an inner surface of the suction shaft 10 can also help maintain the first and second shafts 10, 20 in the mated configuration.

The relative diameters of the suction shaft 10 and the outer shaft 20 can vary depending in part on the particular technique used to mate the shafts 10, 20. As shown in FIG. 11C, for example, the inner passageway 14 of the suction shaft 10 can have a diameter $D_S$ and the inner passageway 24 of the outer shaft 20 can have a diameter $D_2$, with the diameter $D_S$ of the suction shaft 10 being larger than the diameter $D_2$ of the outer shaft 20. This can allow the outer shaft 20 to be received in the inner passageway 14 of the suction shaft 10, as shown. This configuration can also provide additional space for cut tissue to flow from the outer shaft 20 to the suction shaft 10, which can prevent clogging. In another embodiment, the diameter $D_S$ of the suction shaft 10 can be equal to the diameter $D_2$ of the outer shaft 20 such that the distal end 10p of the suction shaft 10 can abut the distal end 20p of the outer shaft 20 when the shafts 10, 20 are in the mated configuration. In another embodiment, the diameter $D_S$ of the suction shaft 10 can be less than or equal to the diameter $D_2$ of the outer shaft 20. For example, the diameter $D_S$ of the suction shaft 10 can gradually increase along the proximal-distal length of the shaft 10. This can result in a diameter at a proximal end of the shaft 10 being larger than the diameter at the distal end 22 of the shaft 10, which can prevent tissue from occluding or obstructing the inner passageway 14 of the suction shaft 10. Each of the shafts 10, 20 can have thin sidewalls in order to maximize the inner passageways 14, 24 and minimize the outer diameter of the shafts 10, 20.

The devices described herein can be used in a variety of surgical procedures for removing tissue and/or reshaping a patient's anatomy, such as knee and shoulder arthroscopy. Although the procedures are described herein with reference to the cutting assembly of FIGS. 1-3 and the suctioning assembly of FIG. 7, other devices can be used to perform the procedure. Additionally, although soft tissue is shown being cut and suctioned, fluid and/or hard tissue, e.g. bone, can additionally or alternatively be cut and suctioned. In an exemplary embodiment, the surgical procedure can be minimally invasive procedure. However, the devices can be used in an open surgical procedure and in a robotic surgical procedure.

The surgical procedure can include preparing the patient for surgery using standard techniques. One or more incisions can be formed at various locations in a patient. For example, the incisions can be formed using a cutting tool. Alternatively, the incisions can be formed by piercing skin of the patient with the distal end of the cutting assembly, then advancing the cutting assembly through a surgical site and out of the opposite skin surface of a patient to form two opposed incisions. In a minimally invasive procedure, one or more access devices (not shown), e.g., a cannula, a trocar, etc., can be advanced through an incision formed in the patient and can be positioned near a surgical site. In another embodiment, one or more of the shafts 10, 20 can be inserted directly into an incision. The opening, incision, or access device is also referred to herein as an "access portal." The access portals can be positioned in various ways relative to a surgical site, e.g., a joint. More specifically, when a device is utilized to perform knee arthroscopy, such as to debride a slightly frayed meniscus, the portals could be located anterolateral, anteromedial, and posterolateral. In one embodiment, the access portals can positioned such that a longitudinal axis of the suction shaft 10 can be substantially aligned with a longitudinal axis of the outer shaft 20. This can facilitate mating of the distal ends 10d, 20d of the shafts 10, 20 when the shafts 10, 20 are positioned in a surgical site, as will be discussed below. The access portal can have a diameter sized to receive the shafts 10, 20 therein, and in some embodiments, an inner diameter of the access portal can be less than or equal to 2 mm.

Figure 12A:
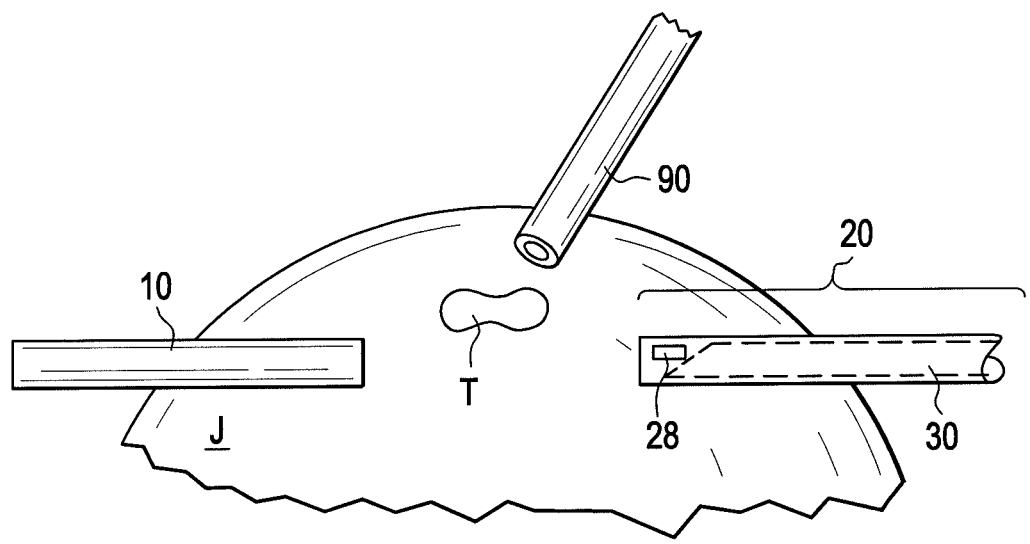
FIG. 12A is a perspective view of a suction shaft, an outer shaft, and a scope inserted through three access portals and positioned near a target tissue.

The outer shaft 20 of the cutting assembly 200 and the suction shaft 10 of the suction assembly 100 can be inserted into the body through one or more of the access portals, and the shafts 10, 20 can be moved distally to approach a surgical site. FIG. 12A illustrates exemplary components positioned in a joint J, near a target tissue T. As shown in FIG. 12A, when the shafts 10, 20 are positioned in a body, a longitudinal axis of the suction shaft 10 can be substantially parallel to a longitudinal axis of the cutting element 30 and, in some embodiments, can be coaxial with the longitudinal axis of the cutting element 30. A scoping device 90, such as an endoscope, can be positioned near the shafts 10, 20, and the scoping device 90 can be configured to acquire images of the surgical site to facilitate visualization of the site. The suction shaft 10, the outer shaft 20, and the scoping device 90 can surround the tissue T in various configurations. In the illustrated embodiment, the shafts 10, 20 are angularly offset from the scoping device 90 by about 120 degrees. However, the components can be positioned in any configuration relative to the tissue T provided that the shafts 10, 20 can be mated together. By way of non-limiting example, the surgical site can also be visualized using fluoroscopy, X-ray, or other visualization techniques known in the art.

Figure 12B:
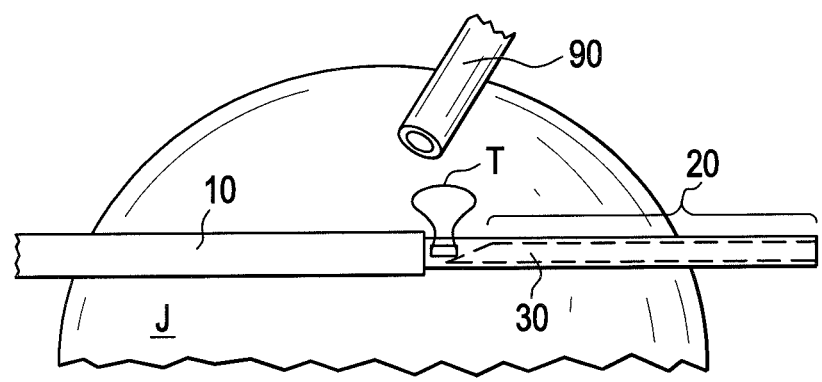
FIG. 12B is a perspective view of the shafts shown in FIG. 12A mated together and activated to suction the target tissue into the device.

With the first and second shafts 10, 20 positioned in the surgical site, the distal end 10d of the suction shaft 10 can be mated with the distal end 20d of the outer shaft 20, as shown in FIG. 12B. The scoping device 90 can be used, for example, to confirm that the distal ends 10d, 20d of the shafts 10, 20 are properly mated together. Depending on the type of connection utilized to join the shafts 10, 20, manual or tactile feel can additionally or alternatively be used to confirm that the shafts 10, 20 are mated. If desired, after the shafts 10, 20 are joined, they can be moved as a unit until the window 28 is positioned in proximity to a targeted tissue. The positioning of the shafts 10, relative to the window 28 can be monitored using the scoping device.

In another embodiment, the shafts 10, 20 can be mated outside of the body, and introduced into a surgical site, e.g. a joint, in the mated configuration. For example, the shafts 10, 20 can be substantially flexible and slightly curved along their length such that the distal ends 10d, 20d can be mated and introduced into a single access portal without kinking or otherwise inhibiting cutting and suctioning of tissue.

Figure 13A:
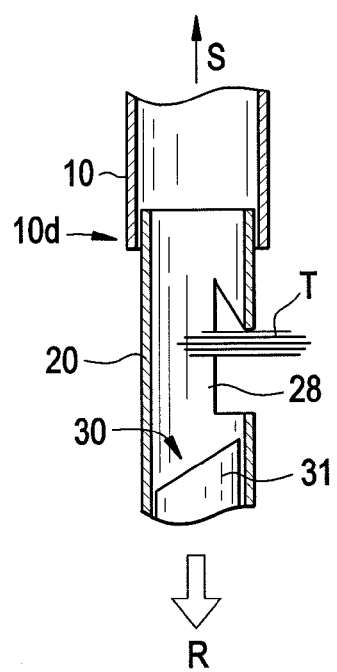
FIG. 13A is a side cross-sectional view of the suction shaft and outer shaft mated together with tissue extending through the window formed in the outer shaft.
Figure 13B:
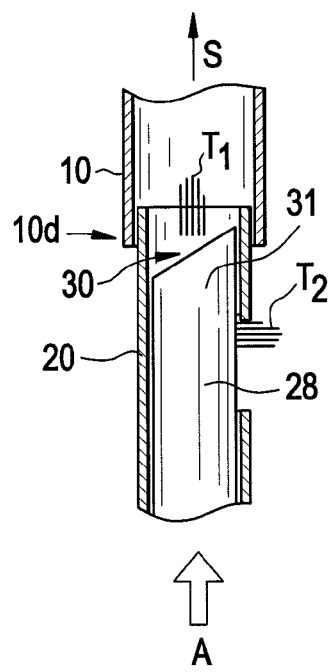
FIG. 13B is a side cross-sectional view of the device of FIG. 13A showing the cutting element being advanced to cut tissue disposed through the window.
Figure 13C:
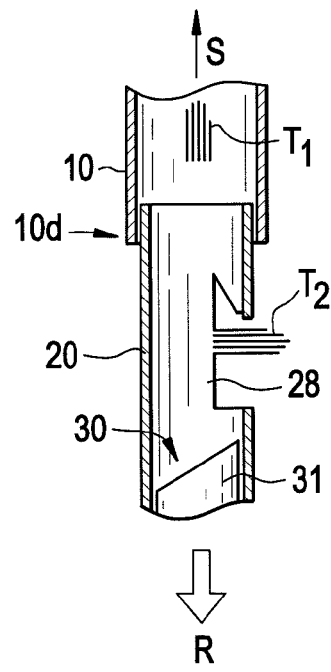
FIG. 13C is a side cross-sectional view of the shaver of FIGS. 13A and 13B with the cutting element retracted and cut tissue flowing through the suction shaft, toward a proximal end of the suction shaft.

FIGS. 13A-13C depict the suctioning and cutting assemblies 100, 200 of FIG. 1 engaged to cut tissue. In particular, the inner shaft 31 is shown being advanced and retracted to position the cutting element 30 on the distal end 31d thereof in a desired location relative to the window 28. For example, FIG. 13A illustrates the tissue T being suctioned through the window 28 and extending into the suction shaft 10. A suction force S can be applied to the proximal end 10p of the suction shaft 10, as indicated by the thin arrow, such that the suction force S can draw the tissue T through the window 28 and toward the proximal end 10p of the suction shaft 10. The cutting element 30 can be initially positioned proximal to the window 28 formed in the outer shaft 20, also referred to herein as the "retracted position." In the retracted position, the inner shaft 31 and the cutting element 30 can be positioned to allow the tissue T to pass through the window 28 without being partially or entirely obstructed by the cutting element 30.

The inner shaft 31 can move from the retracted position to an "extended position," as shown in FIG. 13B. An advancing force A can be applied to the inner shaft to move the cutting element 30 toward the distal end 20d of the outer shaft 20, as indicated by the arrow, such that the cutting element advances distally past the window 28 to cut the tissue T disposed in the window 28. A suctioning force S can be applied to the suction shaft 10, as shown, to cause a first piece of cut tissue $T_1$ to move distally out of the outer shaft 20, and to be drawn proximally into the distal end 10d of the suction shaft 10. The tissue T will continue to move toward the proximal end 10p of the suction shaft 10. A retraction force R can be applied to the inner shaft 31, which can move the cutting element 30 from the extended position to the retracted position to provide adequate space for the tissue to flow through the window 28. A second piece of cut tissue $T_2$ can be drawn in the window 28, and the procedure can be repeated to cut additional tissue.

Figure 14:
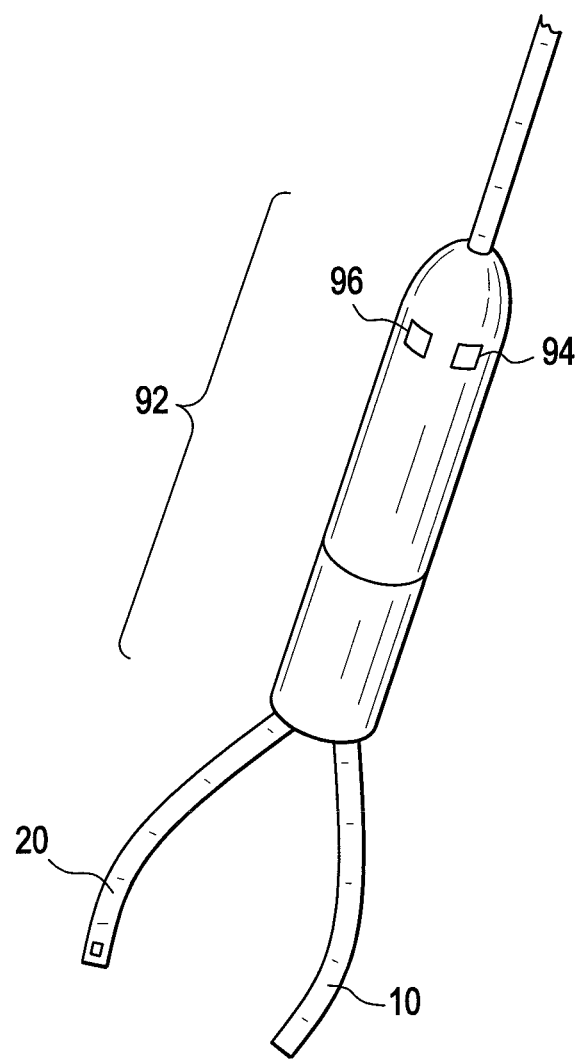
FIG. 14 is a perspective view of another embodiment of a device having suctioning and cutting assemblies integrated into a single hand piece.

The devices describes herein can vary in other ways. For example, FIG. 14 illustrates an embodiment of a device 600 that has a suction shaft 10 and an outer shaft 20 joined to a single hand piece 92. As shown, the proximal end 10p of the suction shaft 10 can be coupled to the distal end 92d of the hand piece 92, and the proximal end 20p of the outer shaft 20 can also be coupled to the distal end 92d of the hand piece 92. Because the shafts 10, 20 are separable, the ends can be joined after each of the shafts 10, 20 are inserted into a body through the same or separate access portals. As in the previous embodiments, the hand piece 92 can house various components for applying suction to the device and/or moving the cutting element 30 relative to the outer shaft 20, and can include a plurality of actuators 94, 96. For example, a first actuator 94 can cause the cutting element 30 to move relative to the shaft 20, and a second actuator 96 can cause suction to be applied to the suction shaft 10. The hand piece 92 can include a steering assembly, such as cables, coupled to the shafts 10, 20 to allow a user to manipulate the distal ends 10d, 20d of the shafts 10, 20 when the device is positioned in a surgical site.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the cutting assembly, suctioning assembly, hand piece, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a suction shaft having an inner passageway extending therethrough between proximal and distal ends thereof, the suction shaft being configured to couple to a vacuum source to apply suction through the inner passageway; and
   a cutting assembly comprising:
      an outer shaft having an inner passageway extending therethrough between proximal and distal ends thereof, the outer shaft having a window formed through a sidewall thereof adjacent to the distal end, and
      an inner shaft having a cutting element at a distal end thereof, the inner shaft being slidably disposed within the outer shaft such that the cutting element is movable relative to the window to allow tissue extending through the window and into the inner passageway of the outer shaft to be cut by the cutting element; and wherein the distal end of the outer shaft is receivable within the distal end of the suction shaft to mate the outer shaft and the suction shaft such that, when suction is applied through the inner passageway in the suction shaft, tissue cut by the cutting element is suctioned out of the distal end of the outer shaft and into the distal end of the suction shaft and can flow in a proximal direction through the inner passageway of the suction shaft.

2. The device of claim 1, wherein the inner shaft is non-cannulated.

3. The device of claim 1, wherein the cutting element is formed on a distal-facing surface of the inner shaft.

4. The device of claim 1, wherein the cutting element is configured to move longitudinally within the inner passageway along a longitudinal axis of the outer shaft to cut the tissue extending through the window and into the inner passageway.

5. The device of claim 1, wherein the cutting element is configured to rotate within the inner passageway about a longitudinal axis of the outer shaft to cut the tissue extending through the window and into the inner passageway.

6. The device of claim 1, wherein the window includes a cutting feature formed thereon.

7. The device of claim 6, wherein the cutting feature is formed on a distal edge of the window such that the cutting element faces the cutting feature when the cutting element moves within the outer shaft.

8. The device of claim 1, further comprising a suction mechanism configured to apply a suction force within the inner passageway of the suction shaft to cause the tissue cut by the cutting element within the inner passageway to flow in the proximal direction through the inner passageway of the suction shaft.

9. The device of claim 1, wherein an outer diameter of the outer shaft is less than about 2 mm.

10. The device of claim 1, wherein an outer diameter of the suction shaft is less than about 2 mm.

11. A surgical device, comprising:
a suction shaft having an inner passageway extending therethrough between proximal and distal ends thereof, the suction shaft being configured to couple to a vacuum source to apply suction through the inner passageway; and
a cutting assembly comprising:
an outer shaft having an inner passageway extending therethrough between proximal and distal ends thereof, the outer shaft having a window formed through a sidewall thereof adjacent to the distal end, and
an inner shaft having a cutting element at a distal end thereof, the inner shaft being slidably disposed within the outer shaft such that the cutting element is movable relative to the window to allow tissue extending through the window and into the inner passageway of the outer shaft to be cut by the cutting element; and
wherein the distal end of the outer shaft is configured to mate with the distal end of the suction shaft such that, when suction is applied through the inner passageway in the suction shaft, tissue cut by the cutting element is suctioned distally out of the distal end of the outer shaft and into the distal end of the suction shaft and flows in a proximal direction through the inner passageway of the suction shaft.

12. The device of claim 11, wherein the inner shaft is solid.

13. The device of claim 11, wherein the cutting element is configured to move longitudinally within the inner passageway along a longitudinal axis of the outer shaft to cut the tissue extending through the window and into the inner passageway.

14. The device of claim 11, wherein an outer diameter of the outer shaft is less than about 2 mm.

15. The device of claim 11, wherein an outer diameter of the suction shaft is less than about 2 mm.

16. The device of claim 11, wherein the window includes a cutting feature formed thereon.

17. The device of claim 11, further comprising a first handpiece coupled to a proximal end of the suction shaft and a second handpiece coupled to a proximal end of the cutting assembly.

* * * * *